United States Patent [19]

Stach

[11] 3,961,050
[45] June 1, 1976

[54] INSECTICIDAL COMPOSITIONS AND METHODS OF KILLING INSECTS USING BENZYLTHIOMETHYLENEPHOSPHONAMIDATES AND PHOSPHORAMIDATES

[75] Inventor: Leonard J. Stach, Riverside, Ill.

[73] Assignee: Velsicol Chemical Corporation, Chicago, Ill.

[22] Filed: May 16, 1975

[21] Appl. No.: 578,059

Related U.S. Application Data

[62] Division of Ser. No. 485,190, July 1, 1974, Pat. No. 3,911,057.

[52] U.S. Cl. ............................. 424/216; 424/DIG. 8
[51] Int. Cl.² ............................................ A01N 9/36
[58] Field of Search ...................... 424/216, DIG. 8

[56] References Cited
UNITED STATES PATENTS
3,328,495   6/1967   Anders et al. ................. 260/948 X OTHER PUBLICATIONS
Alimov et al., Chem. Abst., vol. 63, (1965), 13060h.

Primary Examiner—Jerome D. Goldberg
Assistant Examiner—Allen J. Robinson
Attorney, Agent, or Firm—Robert J. Schwarz; Dietmar H. Olesch

[57] ABSTRACT

This invention discloses compounds of the formula

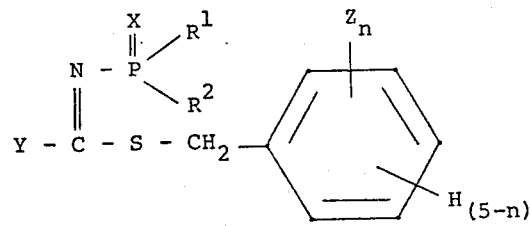

wherein Y is selected from the group consisting of hydrogen and alkyl of from 1 to 3 carbon atoms; X is selected from the group consisting of oxygen and sulfur; $R^1$ and $R^2$ are independently selected from the group consisting of alkyl, alkoxy and alkylthio, provided a maximum of one of $R^1$ and $R^2$ is alkyl; and Z is selected from the group consisting of alkyl, halogen, haloalkyl and nitro. Further disclosed are insecticidal compositions utilizing the compounds of the foregoing description.

2 Claims, No Drawings

INSECTICIDAL COMPOSITIONS AND METHODS OF KILLING INSECTS USING N-BENZYLTHIOMETHYLENEPHOSPHONAMIDATES AND PHOSPHORAMIDATES

This application is a divisional of copending application Ser. No. 485,190, filed July 1, 1974 now U.S. Pat. No. 3,911,057, issued Oct. 7, 1975.

This invention relates to new compositions of matter and more specifically relates to new compounds of the formula

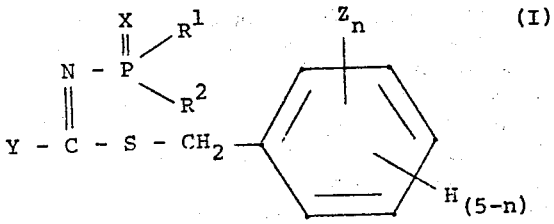

wherein Y is selected from the group consisting of hydrogen and alkyl of from 1 to 3 carbon atoms; X is selected from the group consisting of oxygen and sulfur; $R^1$ and $R^2$ are independently selected from the group consisting of alkyl, alkoxy and alkylthio, provided a maximum of one of $R^1$ and $R^2$ is alkyl; and Z is selected from the group consisting of alkyl, halogen, haloalkyl and nitro.

The compounds of the present invention are useful as insecticides.

In a preferred embodiment of this invention Y is lower alkyl and $R^1$ and $R^2$ are independently selected from the group consisting of lower alkyl, lower alkoxy and lower alkylthio. The term lower as used herein designates a straight or branched carbon chain of up to six carbon atoms.

The compounds of the present invention can be prepared by reacting a thioimidate hydrochloride of the formula

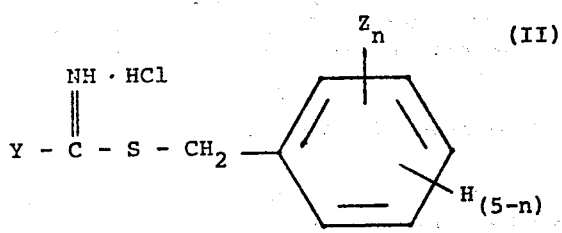

wherein Y and Z are as heretofore described with a chlorophosphorus compound of the formula

wherein X, $R^1$ and $R^2$ are as heretofore described. This reaction can be effected by first precooling a mixture of the compound of formula II dissolved in an inert organic solvent such as methylene chloride and aqueous potassium carbonate to a temperature ranging from about 0°C to about 40°C. A solution of a compound of formula III in an inert solvent such as methylene chloride can then be slowly added with stirring while maintaining the reaction temperature. After the addition is completed the mixture can be allowed to warm to room temperature and can be stirred for an additional period of up to about 6 hours to ensure completion of the reaction. Water can then be added to the reaction mixture to dissolve inorganic salts, if necessary, and the aqueous phase can be separated from the organic phase. The organic phase can then be further washed with water and dried over anhydrous magnesium sulphate. The dried solution can then be stripped of solvent to yield the desired product as a residue.

The compounds of the present invention having the formula

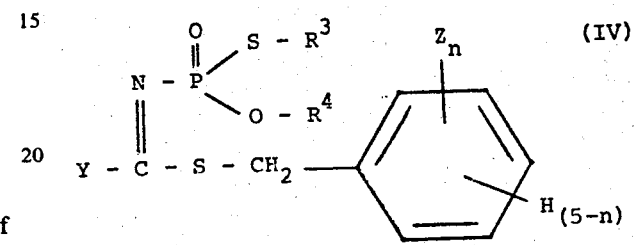

wherein $R^3$ and $R^4$ are each alkyl and Y, Z and n are as heretofore described can be prepared by isomerizing a corresponding compound of the formula

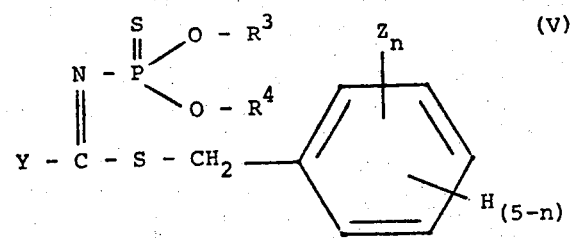

wherein $R^3$ and $R^4$ are alkyl and Y, Z and n are as heretofore described. This isomerization can be effected by heating the compound at a temperature ranging from about 25°C to about 65°C in the presence of a catalytic amount of dimethyl sulphate or in refluxing methyl iodide for a period of from about 2 to about 48 hours. After this time the reaction mixture can be subjected to vacuum stripping to remove unreacted catalyst and to yield the desired product.

The thioimidate hydrochlorides of formula II when not available can be prepared by reacting a thioalkanamide of the formula

wherein Y is as heretofore described with a benzyl chloride of the formula

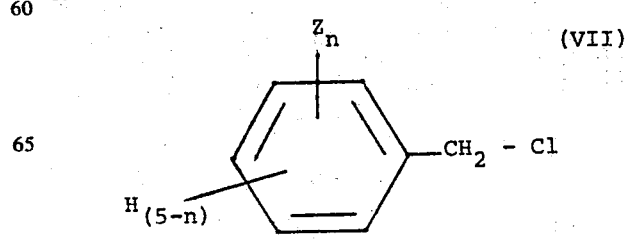

wherein Z and n are as heretofore described. This reaction can be effected by heating a solution of the amide of formula VI in anhydrous toluene at reflux and slowly adding the benzyl chloride of formula VII thereto. After the addition is completed heating at reflux can be continued with stirring for a period of from about 8 to about 24 hours. After this time the reaction mixture can be cooled to room temperature and the desired product can be recovered by filtration if it forms as a precipitate or upon evaporation of the toluene if soluble therein.

Exemplary chlorophosphorus compounds of formula III useful in preparing the compounds of the instant invention are O,O-dimethyl chlorophosphate, O,O-diethyl chlorophosphate, O,O-dipropyl chlorophosphate, O,O-dibutyl chlorophosphate, O,O-dipentyl chlorophosphate, O,O-dihexyl chlorophosphate, O,O-dimethyl chlorothionophosphate, O,O-diethyl chlorothionophosphate, O,O-dipropyl chlorothionophosphate, O,O-dibutyl chlorothionophosphate, S,S-dimethyl chlorodithiolophosphate, S,S-diethyl chlorodithiolophosphate, S,S-dipropyl chlorodithiolophosphate, S,S-dihexyl chlorodithiolophosphate, S,S-dimethyl chlorotrithiophosphate, S,S-diethyl chlorotrithiophosphate, S-methyl S-ethyl chlorotrithiophosphate, S-methyl S-propyl chlorotrithiophosphate, S,S-dihexyl chlorotrithiophosphate, methyl chlorophosphonate, ethyl chlorophosphonate, propyl chlorophosphonate, hexyl chlorophosphonate and the like.

Useful thioamides of formula VI for preparing the compounds of this invention are thioacetamide, thiopropionamide and thiobutyramide.

Exemplary benzyl chlorides of formula VII are benzyl chloride, 2-methylbenzyl chloride, 3-ethylbenzyl chloride, 4-propylbenzyl chloride, 4-hexylbenzyl chloride, 3-chlorobenzyl chloride, 3-bromobenzyl chloride, 4-fluorobenzyl chloride, 4-iodobenzyl chloride, 3,4-dichlorobenzyl chloride, 3,4-dibromobenzyl chloride, 2,4,5-trichlorobenzyl chloride, 4-trifluoromethylbenzyl chloride, 4-chloromethylbenzyl chloride, 3-nitrobenzyl chloride, 3,5-dinitrobenzyl chloride, 2-methyl-4-chlorobenzyl chloride and the like.

The manner in which the compounds of this invention can be prepared is more specifically illustrated in the following examples:

EXAMPLE 1

Preparation of S-Benzyl Thioacetimidate Hydrochloride

Benzene (150 ml) was charged into a 300 ml reaction flask equipped with a condenser and Dean-Stark trap. The benzene was dried by azeotropic distillation. The dried benzene was then cooled to room temperature under a calcium chloride drying tube and thioacetamide (0.15 mole) was added thereto. This mixture was heated a reflux and benzyl chloride (0.15 mole) was slowly added with stirring. After the addition was completed heating at reflux and stirring were continued for a period of about 18 hours. After this time the mixture was cooled to room temperature and filtered to recover the precipitate that formed. The precipitate was then washed with benzene and with ether to yield the desired product S-benzyl thioacetimidate hydrochloride having a melt point of 159° to 161°C.

EXAMPLE 2

Preparation of O,O-Dimethyl N-[(1-Methyl-1-benzylthio)methylene]thionophosphoramidate Potassium carbonate (16.6 grams; 0.12 mole), water (25 ml) and methylene chloride (75 ml) were charged into a 300 ml glass reaction vessel equipped with a mechanical stirrer, thermometer and reflux condenser. The mixture was cooled to a temperature of about 10°C and S-benzyl thioacetamide hydrochloride (10.1 grams; 0.05 mole) was added with stirring. The temperature was maintained at 10°C and O,O-dimethyl chlorothionophosphate (9.64 grams; 0.06 mole) dissolved in methylene chloride was added dropwise with stirring. After the addition was completed stirring was continued at a temperature of 10°C for a period of about 60 minutes. The reaction mixture was then allowed to warm to room temperature and was stirred for an additional period of about 3 hours. The reaction mixture was then allowed to stand overnight. Water (20 ml) was then added with stirring. The aqueous phase was separated from the organic phase and the organic phase was washed with water. The washed organic phase was dried over anhydrous magnesium sulphate and then stripped of methylene chloride solvent in a rotary evaporator leaving an oil as the residue. The residue was subjected to vacuum (0.5 mm Hg pressure) to remove unreacted chlorophosphate and to yield the desired product O,O-dimethyl N-[(1-methyl-1-benzylthio)methylene]thionophosphoramidate.

EXAMPLE 3

Preparation of O,S-Dimethyl N-[(1-Methyl-1-benzylthio)methylene]thiolophosphoramidate O,O-Dimethyl N-[(1-methyl-1-benzylthio)methylene]thionophosphoramidate (4.33 grams; 0.015 mole) and dimethyl sulphate (0.10 grams) were charged into a glass reaction vessel equipped with a magnetic stirrer and thermometer. The mixture was heated at a temperature of from about 50°C to 60°C for a period of about 6 hours. The reaction mixture was heated at 40°C in a vacuum of 0.3 mm of Hg to remove unreacted dimethyl sulphate to yield the desired product O,S-dimethyl N-[(1-methyl-1-benzylthio)methylene]thiolophosphoramidate as an amber liquid.

EXAMPLE 4

Preparation of S-(4-Methylbenzyl) Thioacetimidate Hydrochloride

Benzene (150 ml) is charged into a 300 ml glass reaction flask equipped with a reflux condenser and Dean-Stark trap. The benzene is dried by azeotropic distillation. The dried benzene is then cooled to room temperature under a calcium chloride drying tube and thioacetamide (0.15 mole) is added thereto. This mixture is heated at reflux and 4-methylbenzyl chloride (0.15 mol) is slowly added with stirring. After the addition is completed heating at reflux and stirring are continued for a period of about 18 hours. After this time the mixture is cooled to room temperature and filtered to recover the precipitate that formed. The precipitate is then washed with benzene and with ether to yield the desired product S-(4-methylbenzyl) thioacetimidate hydrochloride.

EXAMPLE 5

Preparation of S,S-Diethyl N-[1-Methyl-1-(4-methylbenzylthio)methylene]dithiolophosphoramidate Potassium carbonate (16.6 grams; 0.12 mole), water (25 ml) and methylene chloride (75 ml) are charged into a glass reaction vessel equipped with a mechanical stirrer, thermometer and reflux condenser. The mixture is cooled to a temperature of about 5°C and S-(4-methylbenzyl) thioacetimidate hydrochloride (0.05 mole) is added with stirring. The temperature is maintained at 5°C and S,S-diethyl chlorodithiolophosphate (0.06 mole) dissolved in methylene chloride (30 ml) is added dropwise with stirring. After the addition is completed stirring is continued for a period of about 45 minutes. The reaction mixture is then allowed to warm to room temperature and is stirred for an additional period of about 4 hours. The reaction mixture is then washed with water and is dried over anhydrous magnesium sulphate. The dried solution is stripped of methylene chloride under reduced pressure to yield the desired product S,S-diethyl N-[1-methyl-1-(4-methylbenzylthio)methylene]dithiolophosphoramidate.

EXAMPLE 6

Preparation of S-(4-Chlorobenzyl) Thioacetimidate Hydrochloride

Benzene (150 ml) is charged into a 300 ml glass reaction flask equipped with a reflux condenser and Dean-Stark trap. The benzene is dried by azeotropic distillation. The dried benzene is then cooled to room temperature under a calcium chloride drying tube and thioacetamide (0.15 mole) is added thereto. This mixture is heated at reflux and 4-chlorobenzyl chloride (0.15 mole) is slowly added with stirring. After the addition is completed heating at reflux and stirring are continued for a period of about 18 hours. After this time the mixture is cooled to room temperature and filtered to recover the precipitate that formed. The precipitate is then washed with benzene and with ether to yield the desired product S-(4-chlorobenzyl) thioacetimidate hydrochloride.

EXAMPLE 7

Preparation of O,O-Dipropyl N-[1-Methyl-1-(4-chlorobenzylthio)methylene]phosphoramidate Potassium carbonate (16.6 grams; 0.12 mole), water (25 ml) and methylene chloride (75 ml) are charged into a glass reaction vessel equipped with a mechanical stirrer, thermometer and reflux condenser. The mixture is cooled to a temperature of about 10°C and S-(4-chlorobenzyl) thioacetamide hydrochloride (0.05 mole) is added with stirring. The temperature is maintained at 10°C and O,O-dipropyl chlorophosphate (0.06 mole) dissolved in methylene chloride (30 ml) is added dropwise with stirring. After the addition is completed stirring is continued for a period of about 60 minutes. The reaction mixture is then allowed to warm to room temperature and is stirred for an additional period of about 2 hours. The reaction mixture is then washed with water and is dried over anhydrous magnesium sulphate. The dried solution is stripped of methylene chloride under reduced pressure to yield the desired product O,O-dipropyl N-[1-methyl-1-(4-chlorobenzylthio)methylene]phosphoramidate.

EXAMPLE 8

Preparation of S-(4-Trifluoromethylbenzyl) Thioacetimidate Hydrochloride

Benzene (150 ml) is charged into a 300 ml glass reaction flask equipped with a reflux condenser and Dean-Stark trap. The benzene is dried by azeotropic distillation. The dried benzene is then cooled to room temperature under a calcium chloride drying tube and thioacetamide (0.15 mole) is added thereto. This mixture is heated at reflux and 4-trifluoromethylbenzyl chloride (0.15 mole) is slowly added with stirring. After the addition is completed heating at reflux and stirring are continued for a period of about 18 hours. After this time the mixture is cooled to room temperature and filtered to recover the precipitate that formed. The precipitate is then washed with benzene and with ether to yield the desired product S-(4-trifluoromethylbenzyl) thioacetimidate hydrochloride.

EXAMPLE 9

Preparation of O,O-Di-n-Butyl N-[1-Methyl-1-(4-trifluoromethylbenzylthio)methylene]phosphoramidate Potassium carbonate (16.6 grams; 0.12 mole), water (25 ml) and methylene chloride (75 ml) are charged into a glass reaction vessel equipped with a mechanical stirrer, thermometer and reflux condenser. The mixture is cooled to a temperature of about 10°C and S-(4-trifluoromethylbenzyl) thioacetimidate hydrochloride (0.05 mole) is added with stirring. The temperature is maintained at 10°C and O,O-di-n-butyl chlorophosphate (0.06 mole) dissolved in methylene chloride (30 ml) is added dropwise with stirring. After the addition is completed stirring is continued for a period of about 60 minutes. The reaction mixture is then allowed to warm to room temperature and is stirred for an additional period of about 3 hours. The reaction mixture is then washed with water and is dried over anhydrous magnesium sulphate. The dried solution is stripped of methylene chloride under reduced pressure to yield the desired product O,O-di-n-butyl N-[1-methyl-1-(4-trifluoromethylbenzylthio)methylene]phosphoramidate.

EXAMPLE 10

Preparation of S-(3-Nitrobenzyl) Thioacetimidate Hydrochloride

Benzene (150 ml) is charged into a 300 ml glass reaction flask equipped with a reflux condenser and Dean-Stark trap. The benzene is dried by azeotropic distillation. The dried benzene is then cooled to room temperature under a calcium chloride drying tube and thioacetamide (0.15 mole) is added thereto. This mixture is heated at reflux and 3-nitrobenzyl chloride (0.15 mole) is slowly added with stirring. After the addition is completed heating at reflux and stirring are continued for a period of about 18 hours. After this time the mixture is cooled to room temperature and filtered to recover the precipitate that formed. The precipitate is then washed with benzene and with ether to yield the desired product S-(3-nitrobenzyl) thioacetimidate hydrochloride.

EXAMPLE 11

Preparation of S-Methyl N-[1-Methyl-1-(3-nitrobenzylthio)methylene]methylthiolophosphonamidate Potassium carbonate (16.6 grams; 0.12 mole), water (25 ml) and methylene chloride (75 ml) are charged into a glass reaction vessel equipped with a mechanical stirrer, thermometer and reflux condenser. The mixture is cooled to a temperature of about 10°C and S-(3-nitrobenzyl) thioacetimidate hydrochloride (0.05 mole) is added with stirring. The temperature is maintained at 10°C and S-methyl methylchlorothiolophosphonate (0.06 mole) dissolved in methylene chloride (30 ml) is added dropwise with stirring. After the addition is completed stirring is continued for a period of about 50 minutes. The reaction mixture is then allowed to warm to room temperature and is stirred for an additional period of about 6 hours. The reaction mixture is then wased with water and is dried over anhydrous magnesium sulphate. The dried solution is stripped of methylene chloride under reduced pressure to yield the desired product S-methyl N-[1-methyl-1-(3-nitrobenzylthio)methylene]methylthiolophosphonamidate.

EXAMPLE 12

Preparation of S-(3,4-Dichlorobenzyl) Thiopropionimidate Hydrochloride

Benzene (150 ml) is charged into a 300 ml glass reaction flask equipped with a reflux condenser and Dean-Stark trap. The benzene is dried by azeotropic distillation. The dried benzene is then cooled to room temperature under a calcium chloride drying tube and thiopropionamide (0.15 mole) is added thereto. This mixture is heated at reflux and 3,4-dichlorobenzyl chloride (0.15 mole) is slowly added with stirring. After the addition is completed heating at reflux and stirring are continued for a period of about 18 hours. After this time the mixture is cooled to room temperature and filtered to recover the precipitate that formed. The precipitate is then washed with benzene and with ether to yield the desired product S-(3,4-dichlorobenzyl) thiopropionimidate hydrochloride.

EXAMPLE 13

Preparation of O,O-Dimethyl N-[1-Ethyl-1-(3,4-dichlorobenzylthio)methylene]thionophosphoramidate Potassium carbonate (16.6 grams; 0.12 mole), water (25 ml) and methylene chloride (75 ml) are charged into a glass reaction vessel equipped with a mechanical stirrer, thermometer and reflux condenser. The mixture is cooled to a temperature of about 10°C and S-(3,4-dichlorobenzyl) thiopropionimidate hydrochloride (0.05 mole) is added with stirring. The temperature is maintained at 10°C and O,O-dimethyl chlorothionophosphate (0.06 mole) dissolved in methylene chloride (30 ml) is added dropwise with stirring. After the addition is completed stirring is continued for a period of about 60 minutes. The reaction mixture is then allowed to warm to room temperature and is stirred for an additional period of about 4 hours. The reaction mixture is then washed with water and is dried over anhydrous magnesium sulphate. The dried solution is stripped of methylene chloride under reduced pressure to yield the desired product O,O-dimethyl N-[1-ethyl-1-(3,4-dichlorobenzylthio)methylene]thionophosphoramidate.

EXAMPLE 14

Preparation of S-(3-Bromobenzyl) Thiobutyrimidate Hydrochloride

Benzene (150 ml) is charged into a 300 ml glass reaction flask equipped with a reflux condenser and Dean-Stark trap. The benzene is dried by azeotropic distillation. The dried benzene is then cooled to room temperature under a calcium chloride drying tube and thiobutyramide (0.15 mole) is added thereto. This mixture is heated at reflux and 3-bromobenzyl chloride (0.15 mole) is slowly added with stirring. After the addition is completed heating at reflux and stirring are continued for a period of about 18 hours. After this time the mixture is cooled to room temperature and filtered to recover the precipitate that formed. The precipitate is then washed with benzene and with ether to yield the desired product S-(3-bromobenzyl) thiobutyrimidate hydrochloride.

EXAMPLE 15

Preparation of O-Ethyl N-[1-Propyl-1-(4-bromobenzylthio)methylene]ethylphosphonamidate Potassium carbonate (16.6 grams; 0.12 mole), water (25 ml) and methylene chloride (75 ml) are charged into a glass reaction vessel equipped with a mechanical stirrer, thermometer and reflux condenser. The mixture is cooled to a temperature of about 5°C and S-(3-bromobenzyl) thiobutyrimidate hydrochloride (0.05 mole) is added with stirring. The temperature is maintained at 5°C and S-ethyl ethylchlorophosphonate (0.06 mole) dissolved in methylene chloride (30 ml) is added dropwise with stirring. After the addition is completed stirring is continued for a period of about 50 minutes. The reaction mixture is then allowed to warm to room temperature and is stirred for an additional period of about 2 hours. The reaction mixture is then washed with water and is dried over anhydrous magnesium sulphate. The dried solution is stripped of methylene chloride under reduced pressure to yield the desired product O-ethyl N-[1-propyl-1-(4-bromobenzylthio)methylene]ethylphosphonamidate.

EXAMPLE 16

Preparation of O,S-Dimethyl N-[1-Ethyl-1-(3,4-dichlorobenzylthio)methylene]phosphoramidate O,O-Dimethyl N-[1-ethyl-1-(3,4-dichlorobenzylthio)methylene]thionophosphoramidate (0.05 mole) and dimethyl sulphate (0.3 grams) are charged into a glass reaction vessel equipped with a magnetic stirrer and thermometer. The mixture is heated at a temperature of from about 50°C to 60°C for a period of about 6 hours. After this time the resulting product is subjected to a vacuum of 0.3 mm of Hg for a period of 30 minutes to yield the desired product O,S-dimethyl N-[1-ethyl-1-(3,4-dichlorobenzylthio)methylene]phosphoramidate.

Additional compounds within the scope of the present invention which can be prepared by the procedures of the foregoing examples are O,O-dimethyl N-[1-(2-methylbenzylthio)methylene]phosphoramidate, O,O-diethyl N-[1-methyl-1-(3-ethylbenzylthio)methylene]phosphoramidate, O,O-dipropyl N-[1-(4-propylbenzylthio)methylene]phosphoramidate, O,O-dibutyl N-[1-methyl-1-(4-butylbenzylthio)methylene]phosphoramidate, O,O-dipentyl N-[1-(4-pentylbenzylthio)methylene]phosphoramidate, O,O-dihexyl N-[1-methyl-1-(4-hexylbenzylthio)methylene]phosphoramidate, O,O-dimethyl N-[1-methyl-1-(3-bromobenzylthio)methylene]thionophosphoramidate, S,S-dimethyl N-[1-methyl-1-(4-iodobenzylthio)methylene]dithiolophosphoramidate, S,S-diethyl N-[1-methyl-1-(4-fluorobenzylthio)methylene]dithiolophosphoramidate, S,S-dimethyl N-[1-methyl-1-(4-trifluoromethylbenzylthio)methylene]dithiolophosphoramidate, O,S-diethyl N-[1-methyl-1-(4-methylbenzylthio)methylene]thiolophosphoramidate, O-methyl-S-ethyl N-[1-methyl-1-(4- chlorobenzylthio)methylene]thiolophosphoramidate, O,S-diethyl N-[(1-methyl-1-benzylthio)methylene]thiolophosphoramidate, S,S-dimethyl N-[1-methyl-1-(4-chloromethylbenzylthio)methylene]dithiolophosphoramidate, S,S-dimethyl N-[1-methyl-1-(4-β-bromoethylbenzylthio)methylene]dithiolophosphoramidate, S,S-dimethyl N-[1-methyl-1-(4-γ-chloropropylbenzylthio)methylene]dithiolophoshoramidate, O-methyl N-[1-methyl-1-(4-chlorobenzylthio)methylene]methylphosphonamidate, O-ethyl N-[1-methyl-1-(4-nitrobenzylthio)methylene]methylphosphonamidate, O-propyl N-[1-methyl-1-(3,4-dichlorobenzylthio)methylene]methylphosphonamidate, O-butyl N-[1-methyl-1-(2,4,5-trichlorobenzylthio)methylene]ethylphosphonamidate, O-pentyl N-[1-methyl-1-(2-methyl-4-chlorobenzylthio)methylene]propylphosphonamidate, O-hexyl N-[1-methyl-1-(2-ethylbenzylthio)methylene]butylphosphoramidate, S-methyl N-[1-methyl-1-(3,4-dichlorobenzylthio)methylene]hexylthiolophosphonamidate and the like.

For practical use as insecticides, the compounds of this invention are generally incorporated into insecticidal compositions which comprise an inert carrier and an insecticidally toxic amount of such a compound. Such insecticidal compositions, which can also be called formulations, enable the active compound to be applied conveniently to the site of the insect infestation in any desired quantity. These compositions can be solids, such as dusts, granules or wettable powders; or they can be liquids such as solutions, aerosols or emulsifiable concentrates.

For example, dusts can be prepared by grinding and blending the active compound with a solid inert carrier such as the talcs, clays, silicas, pyrophyllite and the like. Granular formulations can be prepared by impregnating the compound, usually dissolved in a suitable solvent, onto and into granulated carriers such as the attapulgites or the vermiculites, usually of a particle size range of from about 0.3 to 1.5 mm. Wettable powders, which can be dispersed in water and/or oil to any desired concentration of the active compound, can be prepared by incorporating wetting agents into concentrated dust compositions.

In some cases the active compounds are sufficiently soluble in common organic solvents such as kerosene or xylene so that they can be used directly as solutions in these solvents. Frequently, solutions of insecticides can be dispersed under superatmospheric pressure as aerosols. However, preferred liquid insecticidal compositions are emulsifiable concentrates, which comprise an active compound according to this invention and as the inert carrier, a solvent and an emulsifier. Such emulsifiable concentrates can be extended with water and/or oil to any desired concentration of active compound for application as sprays to the site of the insect infestation. The emulsifiers most commonly used in these concentrates are nonionic or mixtures of nonionic with anionic surface-active agents.

A typical insecticidal composition according to this invention is illustrated by the following example, in the quantities are in parts by weight.

EXAMPLE 17

Preparation of a Dust

| | |
|---|---|
| Product of Example 2 | 10 |
| Powdered talc | 90 |

The above ingredients are mixed in a mechanical grinder-blender and are ground until a homogeneous, free-flowing dust of the desired particle size is obtained. This dust is suitable for direct application to the site of the insect infestation.

The compounds of this invention can be applied as insecticides in any manner recognized by the art. One method for destroying insects comprises applying to the locus of the insect infestation, an insecticidal composition comprising an inert carrier and, as the essential active ingredient, in a quantity which is toxic to said insects, a compound of the present invention. The concentration of the new compounds of this invention in the insecticidal compositions will vary greatly with the type of formulation and the purpose for which it is designed, but generally the insecticidal compositions will comprise from about 0.05 to about 95 percent by weight of the active compounds of this invention. In a preferred embodiment of this invention, the insecticidal compositions will comprise from about 5 to 75 percent by weight of the active compound. The compositions can also comprise such additional substances as other pesticides, stabilizers, spreaders, deactivators, adhesives, stickers, fertilizers, activators, synergists and the like.

The compounds of the present invention are also useful when combined with other insecticides in the insecticidal compositions heretofore described. These other insecticides can comprise from about 5 to about 95 percent of the active ingredients in the insecticidal compositions. Use of the combinations of these other insecticides with the compounds of the present invention provide insecticidal compositions which are more effective in controlling insects and often provide results unattainable with separate compositions of the individual insecticides. The other insecticides with which the compounds of this invention can be used in the insecticidal compositions to control insects, can include halogenated compounds such as DDT, methoxychlor, TDE, lindane, chlordane, isobenzan, aldrin, dieldrin, heptachlor, endrin, mirex, endosulfon, dicofol and the like; organic phosphorus compounds such as TEPP, schradan, ethion, parathion, methyl parathion, EPN, demeton, carbophenothion, phorate, zinophos, diazinon, malathion, mevinphos, dimethoate, DBD, ronnel, oxydemeton-methyl, dicapthon, chlorothion, phosphamidon, naled, fenthion, trichlorofon, DDVP and the like; organic nitrogen compounds such as dinitro-o-cresol, dinitrocyclohexylphenol, DNB, DNP, binapacril, azobenzene and the like; organic carbamate compounds such as carbaryl, ortho 5353 and the like; organic sulfur compounds such as penothiazine, phenoxathin, lauryl thiocyanate, [bis(2-thiocyanoethyl)ether], isobornyl thiocyanoacetate and the like; as well as such substances usually referred to as fumigants, as hydrogen cyanide, carbon tetrachloride, calcium cyanide, carbon disulfide, ethylene dichloride, propylene dichloride, ethylene dibromide, ethylene oxide, methyl bromide, paradichlorobenzene and the like.

The compounds of the present invention can also be combined with fungicidal and nematocidal chemical compounds to form pesticidal compositions useful for the control of fungi and in some cases soil nematodes as well as insects. Typical examples of such fungicidal chemical compounds are ferbam, nabam, zineb, ziram, thiram, chloranil, dichlone, glyodin, cycloheximide, dinocap, maneb, captan, dodine, PCNB, p-dimethylaminobenzenediazo sodium sulfonate and the like;

while examples of nematocidal compounds are chloropicrin, O,O-diethyl O-(2,4-dichlorophenyl) phosphorothioate, tetrachlorothiophene, dazomet, dibromochloropropane and the like.

The new compounds of this invention can be used in many ways for the control of insects. Insecticides which are to be used as stomach poisons or protective materials can be applied to the surface on which the insects feed or travel. Insecticides which are to be used as contact poisons or eradicants can be applied directly to the body of the insect, as a residual treatment to the surface on which the insect may walk or crawl, or as a fumigant treatment of the air which the insect breathes. In some cases, the compounds applied to the soil or plant surfaces are taken up by the plant, and the insects are poisoned systemically.

The above methods of using insecticides are based on the fact that almost all the injury done by insects is a direct or indirect result of their attempts to secure food. Indeed, the large number of destructive insects can be classified broadly on the basis of their feeding habits. Among the insects which can be effectively controlled by the compounds of the present invention are the chewing insects, such as the Mexican bean beetle and the southern armyworm; the piercing-sucking insects, such as the pea aphid, the cereal leaf beetle, the housefly, the grape leafhopper, the chinch bug, the lygus bug, the oyster shell scale, the California red scale, the Florida red scale, the soft scale and mosquitoes; the internal feeders, including borers, such as the European corn borer, the peach twig borer and the corn earworm, worms or weevils, such as the codling moth, the alfalfa weevil, the cotton boll weevil, the pink boll worm, the plum curculio, the red banded leaf roller, the melonworm, the cabbage looper and the apple maggot, leaf miners such as the apple leaf miner, the birch leaf miner and the beet leaf miner, and gall insects such as the wheat joint worm and the grape phylloxera. Insects which attack below the surface of the ground are classified as subterranean insects and include such destructive pests as the wooly apple aphid, the Japanese beetle, the onion maggot and the corn rootworm.

The quantity of active compound of this invention to be used for insect control will depend on a variety of factors, such as the specific insect involved, intensity of the infestation, weather, type of environment, type of formulation and the like. For example, the application of only one or two ounces of active chemical per acre may be adequate for control of a light infestation of an insect under conditions unfavorable for its feeding, while a pound or more of active compound per acre may be required for the control of a heavy infestation of insects under conditions favorable to their development.

The insecticidal and acaricidal activity of the compounds of this invention was demonstrated in the following test procedures. The results of each of these procedures are set forth in Table I.

Mexican Bean Beetle

Foliar portions of potted Dwarf Horticultural bean plants in first true leaf growth stage are sprayed with test solution containing a compound of this invention at a concentration of 1000 ppm. Immediately thereafter the soil of the potted plants is drenched with an aqueous emulsion of the test compound at a rate of 50 lbs per acre and the pots are placed in holding racks provided with a subterranean water source. Three test plants are used for each test unit. Five third-instar larvae of Mexican Bean Beetle are caged on treated plants for 72 hours. After this time observations are made for insect mortality.

Pea Aphid

Windsor Broad Bean plants grown under greenhouse conditions, in the first true leaf growth stage and in soil of low moisture content are sprayed with test solution containing a compound of this invention at a concentration of 1000 ppm. Immediately thereafter the soil of the potted plants is drenched with an aqueous emulsion of the test compound at a rate of 50 lbs per acre and the pots are placed in holding racks provided with a subterranean water source. Pea aphids (*Macrosiphum pisi*) adults are transferred to the foliar portion of the treated plants and held there for a period of 72 hours. After this time insect mortality is determined by observation in comparison to controls.

Two-Spotted Spider Mite

Potted horticultural beans at growth stage when primary leaves are approximately one inch long are infested with two-spotted spider mites 24 hours prior to treatment, insuring establishment of adults and egg deposition at time of treatment.

The candidate compound is dissolved in a suitable solvent (acetone, methanol or other) or prepared as wettable powders and diluted to appropriate concentrations with deionized water containing wetting and/or dispersing agents as appropriate.

Infested host plants, as above, are sprayed with test solution containing a compound of this invention at a concentration of 1000 ppm. Immediately thereafter the soil of the potted plants is drenched with an aqueous emulsion of the test compound at a rate of 50 lbs per acre and the pots are placed in holding racks provided with a subterranean water source. Mortality is determined 72 hours after treatment by removing and observing one leaf from each plant.

TABLE I

| | Percent Control | |
| | Product of Example 2 | Product of Example 3 |
| --- | --- | --- |
| Mexican Bean Beetle | 100 | 100 |
| Green Pea Aphid | 60 | 100 |
| Two-Spotted Spider Mite | 90 | 80 |

I claim:
1. An insecticidal composition comprising an inert carrier and, as an essential active ingredient, in a quantity toxic to insects, a compound of the formula

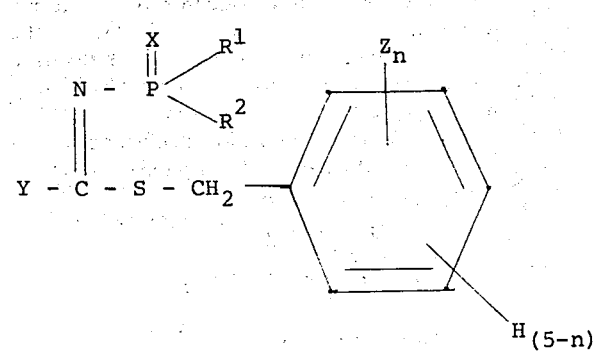

wherein Y is selected from the group consisting of hydrogen and alkyl of from 1 to 3 carbon atoms; X is selected from the group consisting of oxygen and sulfur; $R^1$ and $R^2$ are independently selected from the group consisting of lower alkyl, lower alkoxy, lower alkylthio, provided a maximum of one of $R^1$ and $R^2$ is lower alkyl; and Z is selected from the group consisting of lower alkyl, halogen, lower haloalkyl and nitro.

2. A method of controlling insects which comprises contacting said insects with an insecticidally effective amount of an insecticidal composition of claim 1.

* * * * *